(12) United States Patent
van Dam et al.

(10) Patent No.: US 11,532,101 B2
(45) Date of Patent: Dec. 20, 2022

(54) MARKER ELEMENT AND APPLICATION METHOD WITH ECG

(71) Applicant: Peacs Investments B.V., Nieuwerbrug aan den Rijn (NL)

(72) Inventors: Peter Michael van Dam, Nieuwerbrug aan den Rijn (NL); Eelco Matthias van Dam, Nieuwerbrug aan den Rijn (NL); Samir Alioui, Nieuwerbrug aan den Rijn (NL)

(73) Assignee: Peacs Investments B.V., Nieuwerbrug aan den Rijn (NL)

( * ) Notice: Subject to any disclaimer, the term of this patent is extended or adjusted under 35 U.S.C. 154(b) by 259 days.

(21) Appl. No.: 16/651,804

(22) PCT Filed: Nov. 27, 2018

(86) PCT No.: PCT/NL2018/000021
§ 371 (c)(1),
(2) Date: Mar. 27, 2020

(87) PCT Pub. No.: WO2019/093878
PCT Pub. Date: May 16, 2019

(65) Prior Publication Data
US 2020/0242802 A1 Jul. 30, 2020

(30) Foreign Application Priority Data

Sep. 27, 2017 (NL) ..................... 2019635

(51) Int. Cl.
*G06K 7/14* (2006.01)
*G06T 7/73* (2017.01)
(Continued)

(52) U.S. Cl.
CPC .............. *G06T 7/75* (2017.01); *A61B 5/0062* (2013.01); *A61B 5/0064* (2013.01);
(Continued)

(58) Field of Classification Search
CPC . G06T 7/75; G06T 7/0012; G06T 7/73; G06T 2207/10024; G06T 2207/10028;
(Continued)

(56) References Cited

U.S. PATENT DOCUMENTS 9,286,677 B2    3/2016   Bond et al.
2005/0209525 A1   9/2005   Bojovic et al.
(Continued)

OTHER PUBLICATIONS

Odille et al., "Statistical Variations of Heart Orientation in Healthy Adults", Computing in Cardiology, 2017, 4 pages, vol. 44.
(Continued)

*Primary Examiner* — Ali Bayat
(74) *Attorney, Agent, or Firm* — The Webb Law Firm

(57) ABSTRACT

The present invention relates to a method to be performed by a computing device part of or coupled to an ECG device for applying a marker element in a process of determining positions of a set of ECG electrodes as placed on a human torso relative to a 3D model of a body, preferably a torso model of the torso of the human body. The method includes receiving an imaging information recording relating to the human body from an optical imaging device, preferably a 3D imaging device. The optical imaging information includes imaging information of the exterior of the body, such as imaging information of the exterior of the torso, and imaging information of the marker element. The method also includes performing an image recognition on the imaging information for obtaining a presence determination, preferably a positive or negative determination, of the marker element in the imaging information.

26 Claims, 20 Drawing Sheets

(51) Int. Cl.
*A61B 90/98* (2016.01)
*A61B 5/00* (2006.01)
*G06K 7/10* (2006.01)
*G06T 7/00* (2017.01)
*A61B 5/25* (2021.01)
*A61B 5/318* (2021.01)

(52) U.S. Cl.
CPC .............. *A61B 5/0077* (2013.01); *A61B 5/25* (2021.01); *A61B 5/318* (2021.01); *A61B 5/684* (2013.01); *A61B 5/7405* (2013.01); *A61B 90/98* (2016.02); *G06K 7/10722* (2013.01); *G06K 7/1413* (2013.01); *G06K 7/1417* (2013.01); *G06T 7/0012* (2013.01); *G06T 7/73* (2017.01); *G06T 2207/10024* (2013.01); *G06T 2207/10028* (2013.01); *G06T 2207/20021* (2013.01); *G06T 2207/30048* (2013.01); *G06T 2207/30168* (2013.01); *G06T 2207/30204* (2013.01)

(58) Field of Classification Search
CPC . G06T 2207/20021; G06T 2207/30048; G06T 2207/30168; G06T 2207/30204; A61B 5/0062; A61B 5/0064; A61B 5/0077; A61B 5/25; A61B 5/318; A61B 5/684; A61B 5/7405; A61B 90/98; G06K 7/10722; G06K 7/1413; G06K 7/1417

USPC ........................................................ 382/128
See application file for complete search history.

(56) References Cited

U.S. PATENT DOCUMENTS

| | | | |
|---|---|---|---|
| 2014/0194760 A1* | 7/2014 | Albert | A61B 5/339 600/509 |
| 2015/0154453 A1 | 6/2015 | Wilf | |
| 2016/0213331 A1* | 7/2016 | Gil | A61B 5/25 |
| 2017/0061683 A1 | 3/2017 | Dorin et al. | |
| 2017/0071492 A1 | 3/2017 | van Dam et al. | |
| 2017/0105678 A1* | 4/2017 | Xue | A61B 5/25 |
| 2017/0156615 A1* | 6/2017 | Shirazi | A61B 5/0205 |
| 2018/0035943 A1* | 2/2018 | Shemesh | A61B 5/7203 |
| 2018/0042502 A1 | 2/2018 | Wang et al. | |
| 2019/0038357 A1* | 2/2019 | Adler | A61B 34/10 |

OTHER PUBLICATIONS

Rudy, "Noninvasive Electrocardiographic Imaging of Arrhythmogenic Substrates in Humans", Circulation Research, 2013, pp. 863-874, vol. 112, No. 5.

* cited by examiner

MARKER ELEMENT AND APPLICATION METHOD WITH ECG

CROSS-REFERENCE TO RELATED APPLICATIONS

This application is the United States national phase of International Application No. PCT/NL2018/000021 filed Nov. 27, 2018, and claims priority to The Netherlands Patent Application No. 2019635 filed Sep. 27, 2017, the disclosures of which are hereby incorporated by reference in their entirety.

BACKGROUND OF THE INVENTION

Field of the Invention

The present invention relates to a method for applying a marker element in a process of determining positions of a set of ECG electrodes as placed on a human body relative to a 3D model of a body, preferably a torso model of the human body, more preferably a heart of heart-torso model of the body.

It is an important goal of the present invention to use a marker element in obtaining a match between a 3-D image recording and a model of the thorax that is preferably patient specific and further preferably pre-recorded and available from a database. Furthermore, the localization of ECG electrodes as present on the thorax relative to the 3-D thorax model of the thorax is obtainable. Also the location of the marker element and the ECG electrodes relative to the thorax on the 3-D image recording is preferably obtained. Further preferably, a matching between the 3-D recording of the thorax and the pre-created model allows for localizing the ECG electrodes in the thorax model.

The marker element is preferably located in the 3-D image recording and matched to the corresponding location of the 3-D thorax model. The marker element is purposefully a key locator for accurately relating the positions of ECG electrodes to, both in the 3-D imaging records and the 3-D thorax model.

Description of Related Art

ECG is an in itself well-known imaging technology relating to the heart. However, the ECG technology has its limitations as to the interpretation of obtained data, both within a single imaging session, such as used during a procedure, and between successive imaging sessions over time due to for instance differences in location placement of ECG electrodes leading to variations that will impact imaging results. Such variations lead to inconsistencies in interpretation of the ECG results, and even to inconsistencies in diagnosis based on such ECG results.

It is therefore a goal of the present invention to provide novel means to improve both the use of ECG technology within a single imaging sessions and between successive imaging sessions over time.

To this end, the present invention provides a method for applying a marker element in a process of determining positions of a set of ECG electrodes as placed on a human body relative to a 3D model of a body, preferably a torso model of the human body, more preferably a heart of heart-torso model of the body, the method comprising steps of:
  receiving the model of the body from a storage, and/or directly from an body scanning imaging device, BSID, such as an MRI, CT, PET-CT, ultrasound device, or a database of preferably standardized models,
  receiving imaging information relating to the human body from an optical imaging device, preferably a 3D imaging device, the optical imaging information comprising:
    imaging information of the exterior of the body, at least comprising imaging information of the exterior of the torso,
    imaging information of the marker element, the marker element being arranged in an area comprising an actual position on the body, preferably on the sternum, from a marker element optical imaging device, OID, the ECG electrodes imaging device and the marker element imaging device preferably being the same imaging device,
  performing an image recognition on the imaging information for obtaining a presence determination, preferably a positive or negative determination, of the marker element in the imaging information.

It is a main advantage of the present invention that the presence of a marker element are determinable at any point of performing the ECG measurements the marker element is within optical range of the optical imaging device, such as immediately upon start or throughout performing the ECG measurements. Such presence determination of the marker element provides the basis of use of the marker element in several ways, as embodied in several preferred embodiments, during and after performing a single ECG session or a series of ECG sessions over time. The present invention therefore provides a new tool and the use thereof in a method for, amongst others, improvement of ECG measurements, the use of ECG measurements and during a single ECG session or for the purpose of a series of ECG sessions over time. Such preferred embodiments and advantages of each thereof are described below.

Of importance is that the use of the marker element improves convergence of algorithms to a result in a fast way by pre-elimination of disturbances and parts of the 3-D photo that are not related to the subject.

A further aspect of the invention provides a marker element for use in a method and/or with a system according to any of the preceding claims, the marker element being for placement on an exterior of a body, the marker element comprising:
  a member for taking image recordings thereof placement on the body,
  a recognition pattern for recognition thereof during an ECG session.

The marker element preferably comprises means for emitting a sound or light, further preferably an RFID chip.

A further aspect of the invention provides a computer readable storage medium comprising computer executable instructions for controlling of a computer device in which the computer executable instructions comprise instructions for performing a method according to the invention.

A further aspect of the invention provides a computing device comprising a processor, coupling means for coupling with an ECG device, coupling means for coupling with a 3-D camera and a memory in which the memory comprises computer executable instructions for causing that the processor controls the computing device, in which the computer executable instructions comprise instructions for performing the method according to the invention.

BRIEF DESCRIPTION OF THE DRAWINGS

Further advantages, features and details of the present invention will be further elucidated on the basis of a description of one or more embodiments with reference to the accompanying figures.

SUMMARY OF THE INVENTION

Figure 1A:
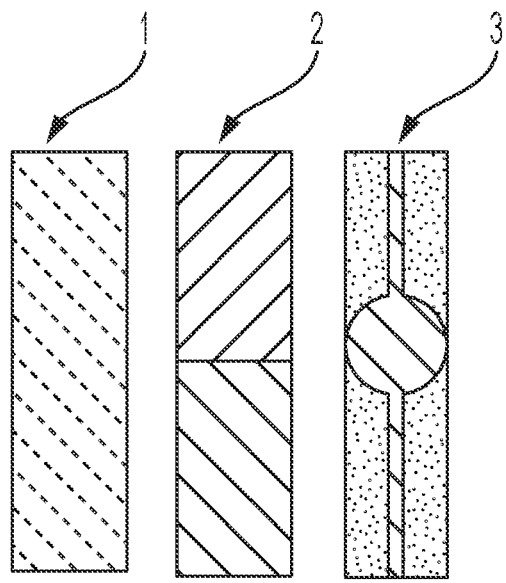
FIG. 1 shows a few preferred embodiments of a marker element according to the present invention.

The present invention is performed using an ECG system as input or an ECG system with features added thereto for embodying the invention. A typical embodiment of a system comprises a computing device with receiving means for receiving from an ECG device the ECG measurements during an ECG session, such as during a procedure or for obtaining data to base a subsequent diagnosis on. The computing device is provided with a processor and memory. The memory comprises program code for enabling the processor to perform the method according to the invention.

Furthermore, the computing device is coupled to a monitor for displaying resulting images. A user interface is also displayed on the monitor for allowing input to be provided. Additional aspects of the user interface is comprised of a keyboard and mouse, touch screen, and all other user preferred in itself known input devices may be coupled to the computer through readily applicable connecting ports.

Furthermore, a 3-D camera is available for taking imaging information recordings from the torso (T). For obtaining the 3-D imaging information recordings, a capability to record from several sides of the torso is preferred. This is obtained by either one camera that is movable to capture images from the top, left and right side of the torso. Alternatively, two or more cameras may be fixedly mounted relative to the position of the torso in order to combine the 3-D imaging information recordings of the two or more cameras.

Furthermore, The computer is preferably connected to a database of 3-D torso models. Such a database of 3-D torso models preferably comprises unique torso models obtained by imaging devices, such as an MRI, CT or sound echo device. Depending on available time and equipment the respective information can advantageously be obtained during the ECG session, before the ECG session or based on historical measuring data for performing of this method.

Preferably, the 3-D photo is recorded by means of a 3-D camera providing a cloud of points in a 3-D space. The cloud of points, or model, represents the subject of the imaging information recording. To this end, the 3-D camera is used to capture an image of a torso of a subject in the form of 3-D information comprising information with respect to depth and color of the subject and of the surroundings of the subject. As indicated in the above, a single camera can be moved relative to the subject, such as along a generally circular line around the torso perpendicular to a longitudinal axis of the subject. Also multiple cameras can be used mounted around the subject for taking the appropriate recordings.

A main subject of the present invention is the use of a marker element to be used as a reference point relative to the torso. According to embodiments such a marking element provides an optically recordable element, such as a surface, perform an input for the analysis of the 3-D imaging information recording and may take the form of a patch, optionally comprising communication electronics providing an identification, having predetermined recognizable characteristics for detecting thereof by means of the computing device executing the appropriate program means. Optionally, the computing device is partly or wholly integrated into the camera device or the ECG device.

Preferably, the position on the thorax is predefined and enables the computing device to match, orient and or detect the thorax in the 3-D imaging information recording under clinical circumstances. By applying the marker, according to the embodiment, the computing device is able to perform an analysis eliminating disturbances, such as blankets, equipment, objects or cables momentarily arranged on top of the person, etc. A quality check of the 3-D photo is preferably based on imaging information relating to the marker element and/or the position of the camera towards the torso and/or marker.

Optionally, when recording a number of images towards different sides towards the body and the marker (for example left, mid and right), this number of images is preferably merged based on perceived marker information and location thereof in the image. Further preferably, the area with clearest image information, for example defined as an area around the marker location, of the number of images based on the determined angle of the camera position to the marker is taken as a basis for this merging.

Alternative embodiments of the marker element comprise features directed at recognition by means of color, signal, patterns, geometry, such as a shape; wherein optionally also through openings in the marker are provided for discerning the skin color.

The marker element provides a means to use as a basis for analysis. Algorithms of analysis are preferably adaptable to a range of predetermined marker types, such as distinguished by means of for example presence of information elements providing directional information such as a pattern of dots, color, shape, dimension, lighting, sound. Preferably, the position of the marker element, or marker elements on the thorax is predefined, for example by having the upper side of the marker element coincide with the upper part of the sternum or suprasternal notch and having the marker elements positioned along the sternum and/or the shoulders.

Several characteristics of several preferred embodiments of the marker element provide distinct advantages. Analysis of any of the optically discernible information, such as the said color or combinations of color, of the marker element provides advantages in permitting the detection of the marker element which enables analysis of an area of the subject where the marker is present. Providing a certain order of color preferably provides information regarding to orientations such as left, right, top, bottom and depth orientations of the subject and allow for such information to be used as inputs in the analysis.

The geometry or shape of the marker element provides the advantage of improved performance of analysis, such as during detection of the marker on the subject.

Characteristics such as the optically discernible pattern, scannable code, bar code or QR code, sound, light or a signal from an RFID chip provided in the marker element each provide advantages in the detection of the marker and advantages in performing the analysis according to the present invention, such as in identifying the marker element on the thorax of the patients.

The marker element represents a reference point towards the algorithm performing the analysis in a way that defines the 3-D space independently of how the recording of the imaging information is performed. That is, independent of which camera is used, what the orientation of the camera is, as the marker is comprised in the imaging information recording. The marker provides a basis for the algorithms to determine the orientation of the marker and based on that create an initial estimate of the orientation of the thorax. If non-preferable outcomes are obtained, information may be outputted as to a change in positioning of the camera are relative to the subject, such as to provide a better alignment with regard to e.g. a longitudinal axis of the torso, or to provide a better alignment relative to the marker element.

Analysis of the external shape of the subject is a further aspect in the marker element is set to improve. In case of e.g. a female subject, algorithms are provisioned to detect the shape of a breast relative to the marker position. Also the location, shape or width of shoulders, sides of the body and/or the length of the sternum body are information elements to use in the analysis as indicated below. Based on this, specific analysis of the 3-D imaging information recording is performed. Advantages thereof are that the time required for performing calculations for the analysis is reduced contributing to real-time usable results. As such, the marker element is preferably the starting point of the comparison between the 3-D imaging information recording and the 3-D model of the torso obtained.

An initial verification step in recording the 3-D imaging information recording comprises verification of the presence of the marker element. Preferably also a verification is made of acceptability of the image due to general photographic circumstances, including lighting situation, of the area or area in a room in which the recording is performed.

Furthermore, the 3-D imaging information recording is generated and verified with respect to the presence of the marker element, whereupon it is saved and used for further analysis.

DESCRIPTION OF THE INVENTION

FIG. 1 shows six preferred embodiments 1, 2, 3 according to the present invention of the marker element. Marker element 1 consists of a blue rectangle allowing for identification based on at least the color and shape. The color allows for identification of the color and the meaning of such color as predetermined. Aspects of analysis of orientation with this embodiment will come from information in the 3-D image recording relating to e.g. the torso. Marker element 2 consists of a rectangle having two areas of color. Such rectangle also provides an analysis as to up and down and left and right sides based on the information of the colors. Therefore, more aspects of analysis can be determined based on the marker element in itself. Marker element 3 consists of a rectangle having a general element of color and a shape defined therein, in this case comprising a vertical line or bar with a circle generally oriented at the middle of the marker element 3.

Figure 1B:
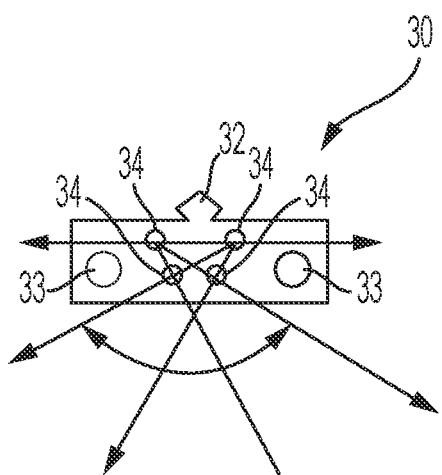
Figure 1C:
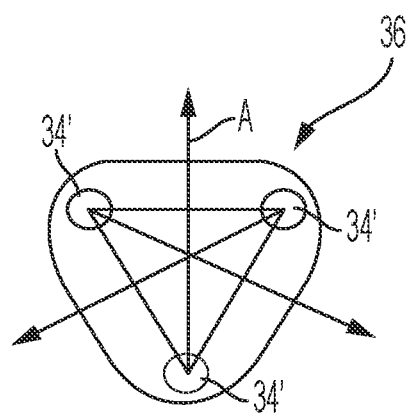
Figure 1D:
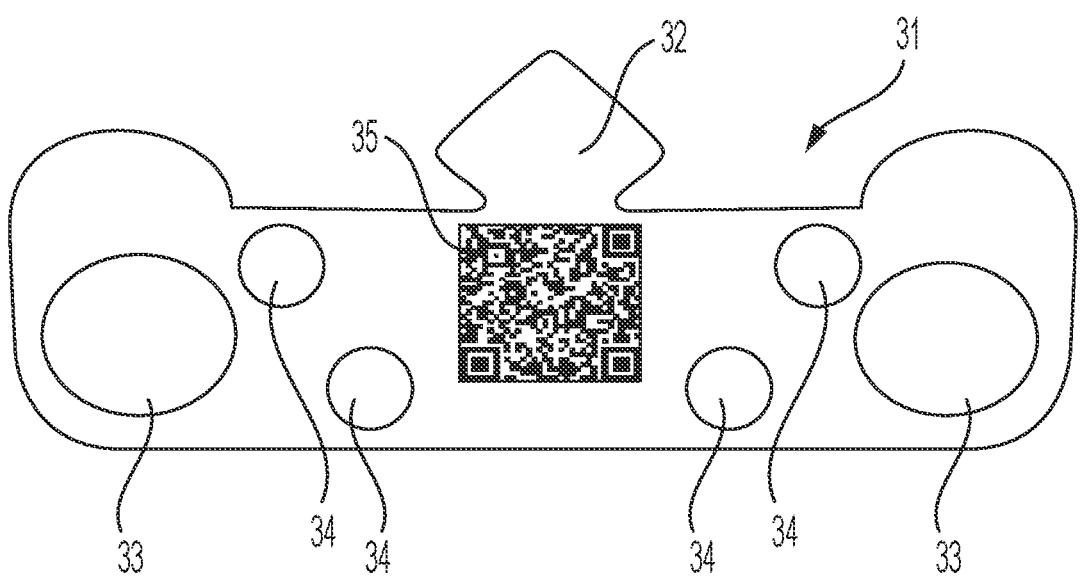

In FIG. 1B, a further preferred embodiment of a marker element (30) according to the present invention is shown. The marker element comprises a generally diamond-shaped extension 32 that extends upwards from the main body of the marking element 30. This generally diamond-shaped extension is intended to be placed on the sternum The marker element is a generally rectangular element comprising several visual elements that are usable for determining presence of a marker element in the imaging information of the torso. A first of those elements is the general shape itself. Another one of those elements is defined by four circles 34 in a generally trapezoidal shape. This shape both helps by recognizing the marker itself and is functional in defining lines that are functional at indicating parts of the torso at which ECG leads of features are to be expected.

Figure 2:
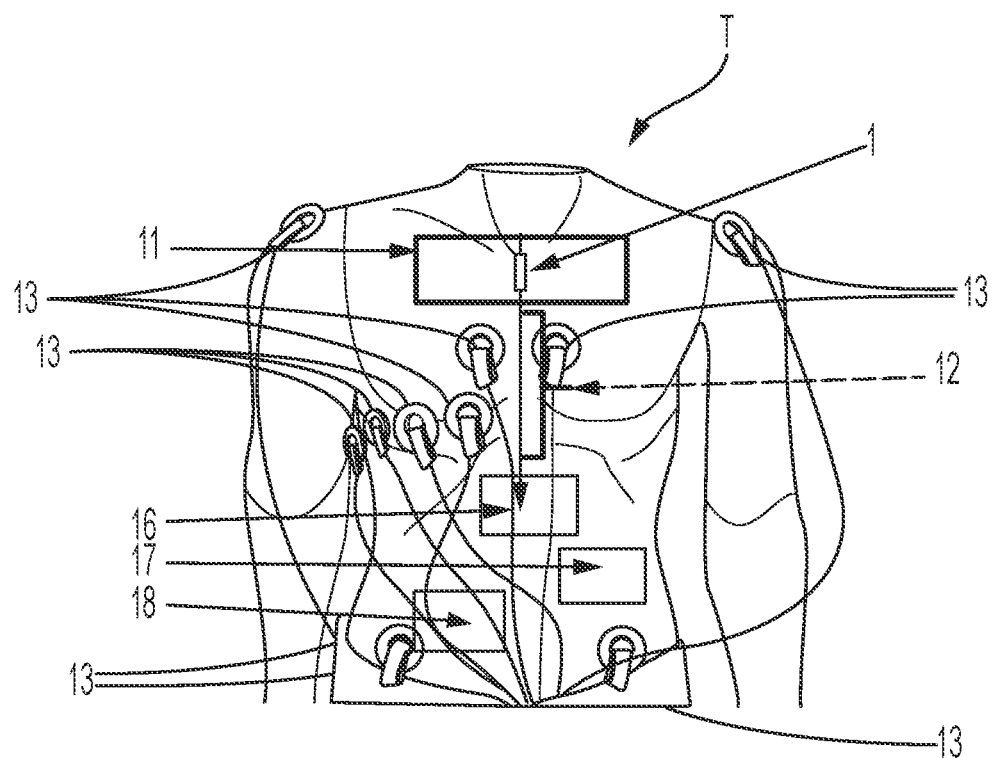
FIG. 2 shows one of the preferred embodiments of the marker element as applied on a torso relative to ECG electrodes also on the torso for performing a method according to a further preferred embodiment.

FIG. 2 is provided to show an overview of a torso with a marker element on the sternum and ECG electrodes oriented on the torso. The quality of the ECG recordings, and comparability of a range of recordings over time is dependent on a correct orientation and/or position or the same orientation and/or position in the several recordings over time.

The present invention has as an important advantage that it becomes possible to relate the position of the ECG electrodes to the position of the marker element and thus to a fixed position on the torso. Furthermore, the present invention enables relating the imaging information recording to the model of the torso. Furthermore, the present invention enables relating the position of the marker element to the model of the torso, furthermore, the present invention enables relating the position of the ECG electrodes to the torso model, preferably wherein the marker element provides a basis for calculating such relation and allowing for calculating such relation very speedily, such as fast enough for providing a result usable within the session, defined as real-time within the context of the present invention.

In an embodiment of the analysis, the 3-D imaging information recording is divided in areas. A main area of analysis is the marker area 11. The marker area 11 is an area defined around a detected marker. Other areas comprise area has 16, 17, 18, which are areas defined to compare parts of the 3-D imaging information recording with the torso model information for reaching a match between those. The electrodes 13 are preferably regular ECG electrodes, preferably recognizable by shape or color for identification thereof, which electrodes are to be matched to the torso model by means of 3D imaging information and the presence of the marker therein.

Figure 3:
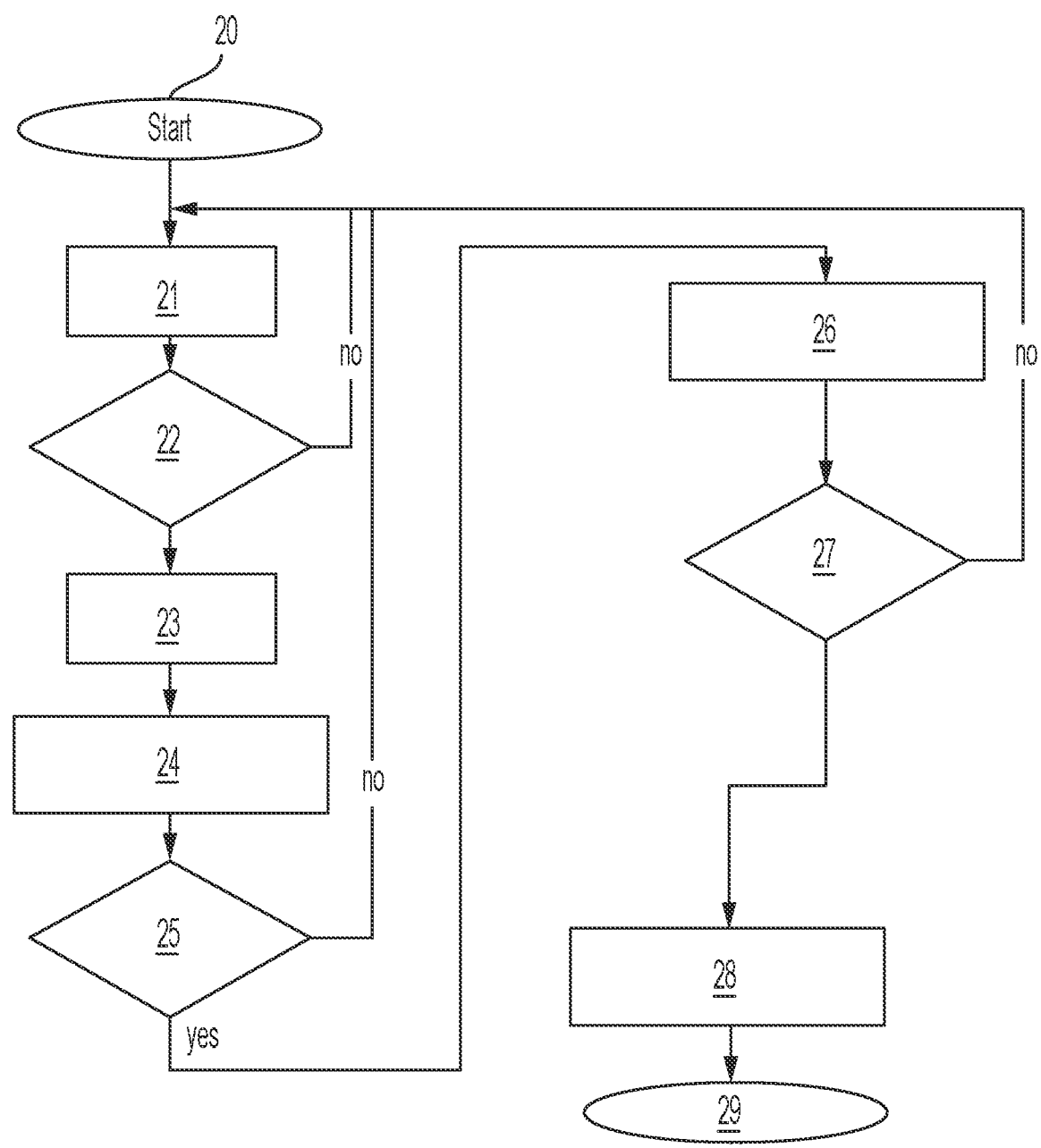
FIG. 3 is a flowchart of a part of a further preferred embodiment according to the present invention relating to the detection of a marker element and ECG electrodes.

FIG. 3 provides a general overview of the method according to an embodiment. Initially the method is started in step 20. In step 21, imaging information as obtained from the 3-D camera is interpreted to assess the presence of a marker. It is preferred that imaging information is recorded in case such presence of a marker is assessed, in order to record usable information. In step 22, it is determined if a marker is present in imaging information. In case there is no marker detected in the imaging information, the method returns to step 21. In case a marker is determined to be detected in step 22 in the imaging information, the imaging information is structured to coordinates, color information and or depth. The result is a cloud of points in step 23.

In step 24, the results of step 23 are divided into areas of analysis, such as areas to be compared with areas of the 3-D torso model in order to provide a quality check. In step 25 it is determined whether enough areas for further analysis are defined. In case it is determined that not enough areas for further analysis are defined, the method returns to step 21. In case it is determined that enough areas for comparison are defined, and as such the quality check of the 3-D imaging information recording provides a positive determination, the method continues in step 26 or the intermediate result is stored for later matching.

In step 26, the preprocessed 3-D imaging information recording is matched to matchable information of the 3-D torso model as obtained. In step 27 it is determined whether a match was possible between the information from the 3-D imaging information recording and the 3-D torso model. In case it is determined that the match was not possible or of inferior quality, the method returns to step 21 in order to reprocess with a new 3-D imaging recording. In case it is determined that the method provided a match of an acceptable quality, such as within certain predetermined limits, in step 28, the electrodes are detected from the 3-D imaging information and matched with the torso model for adding information relating to the electrodes to the 3-D torso model, the method ending in step 29.

Figure 4:
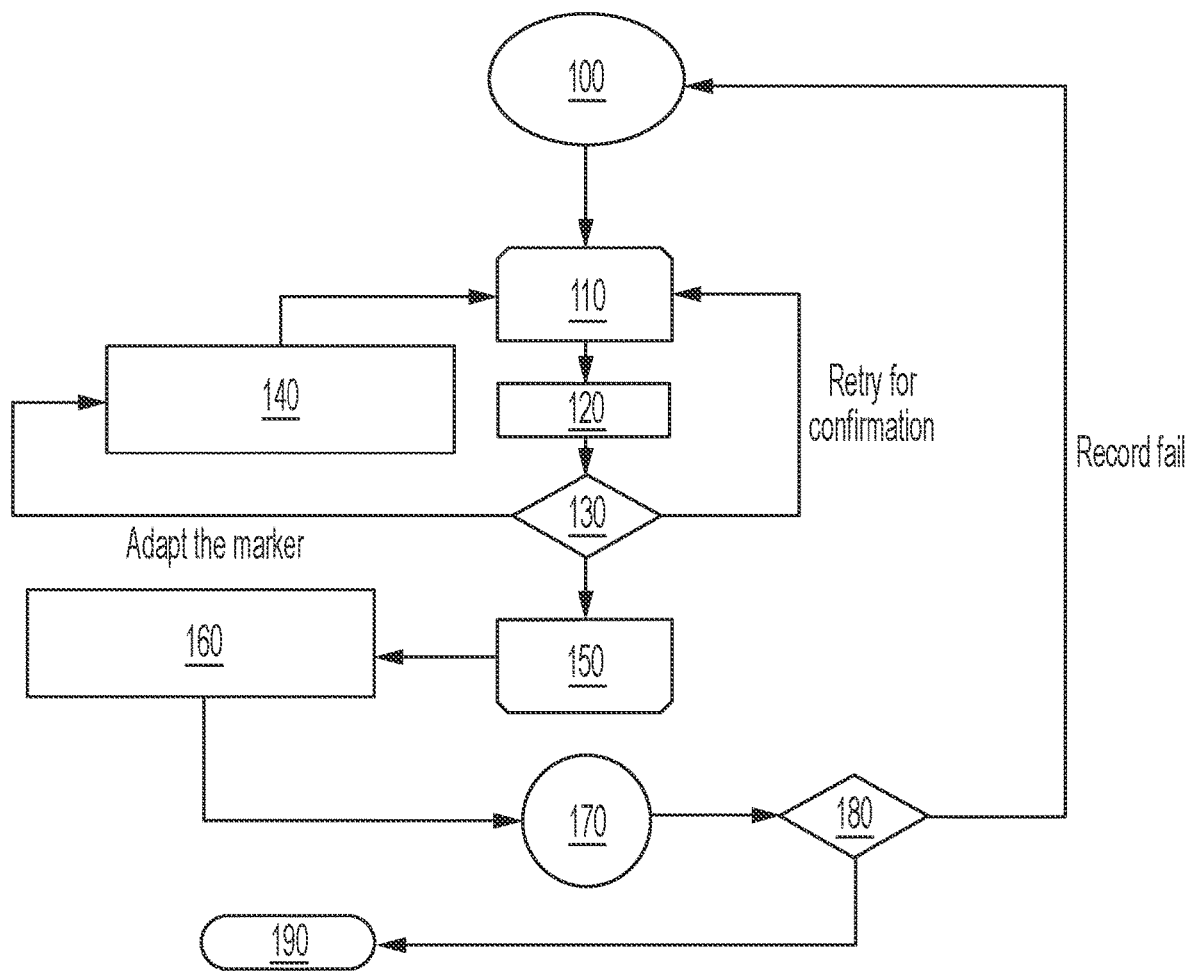
FIG. 4 is a flowchart of a part of a further preferred embodiment according to the present invention relating to detection of a marker and analysis of a 3D image recording.

FIG. 4 provides a further embodiment of the method according to the present invention. The method starts in step 100 as a configuration step for loading resources needed, based on an instruction into the user interface for generating a 3-D image recording. The detection algorithm is initialized by providing characteristics of the marker element used in the respective session. Those characteristics, such as colors, such as blue, green or pink, geometry, such as rectangular, square, triangular, or its dimensions, such as width, depth or height, are retrieved from the database. These characteristics are used for creating groups of points having at least one of the marker description, such as the color.

In step 110, the information relating to the 3-D imaging information is received from the 3-D camera comprising e.g. color, depth and etc. The information is structured to coordinates having color and/or shape information.

In step 120, the 3-D imaging information is prepared for analysis for detecting the marker. The received imaging information is analyzed for the presence of the marker. The marker is preferably present in the marker element tracking area 11 that is displayed, preferably yellow, on a display integrated in the camera or a monitor of the computing device showing the imaging information. Pixels that are received inside the marker element tracking area 11 are added to a list or set with the same criteria. A list is created for each predetermined marker element criterion. This is functional in finding the marker within a set with. Pixels having the same color, such as on the marker will be on the same list.

In step 130, the marker is identified based on the created lists. Information as to the geometry of the marker is extracted from the information of the pixels in the lists. If this is not successful, a calibration is performed with respect to constraints such as circumstances such as light in the room that can influence the colors of the recording. If the marker is found, the method follows in step 140. An example is a marker that is a rectangle, one half centimeter wide, 5 cm high and having a blue-collar. The step of analyzing will identify the list having the pixels providing the rectangular shape, such as by taking four points of the selected list and calculating the angle created by each three points. If the angle is 90°, the distance and the color match, and then the list comprises information relating to the marker.

In step 140, the order of calibration and a zone of calibration is processed. If the marker was not detected, the camera is directed such that the marker is in the marker element area 11. The said calibration is performed and step 130 is repeated. In step 150, it is determined that the 3-D imaging information contains the marker and the 3-D imaging information is recorded. One session according to the present invention may comprise a number of recordings over the duration of the ECG session.

Based on the created 3-D imaging recordings, a full 3-D imaging recording of the torso is created. Images are taken of the torso from several angles, all comprising the marker. For example, the camera is moved by starting capturing from the left part of the torso moving over the torso to the right part of the torso. During such movement of the camera the camera takes a temporary image recording every second after which the recordings are combined to a 3-D image recording of the full torso. All individual recordings are processed as described in the above in order to assess the presence of the marker.

In step 170, the 3-D image recording of the full torso is verified. In case the combination of the sip recordings electrodes to deformations due to inconsistent camera moving, the recordings have to be taken again by repeating the above steps.

Figure 5:
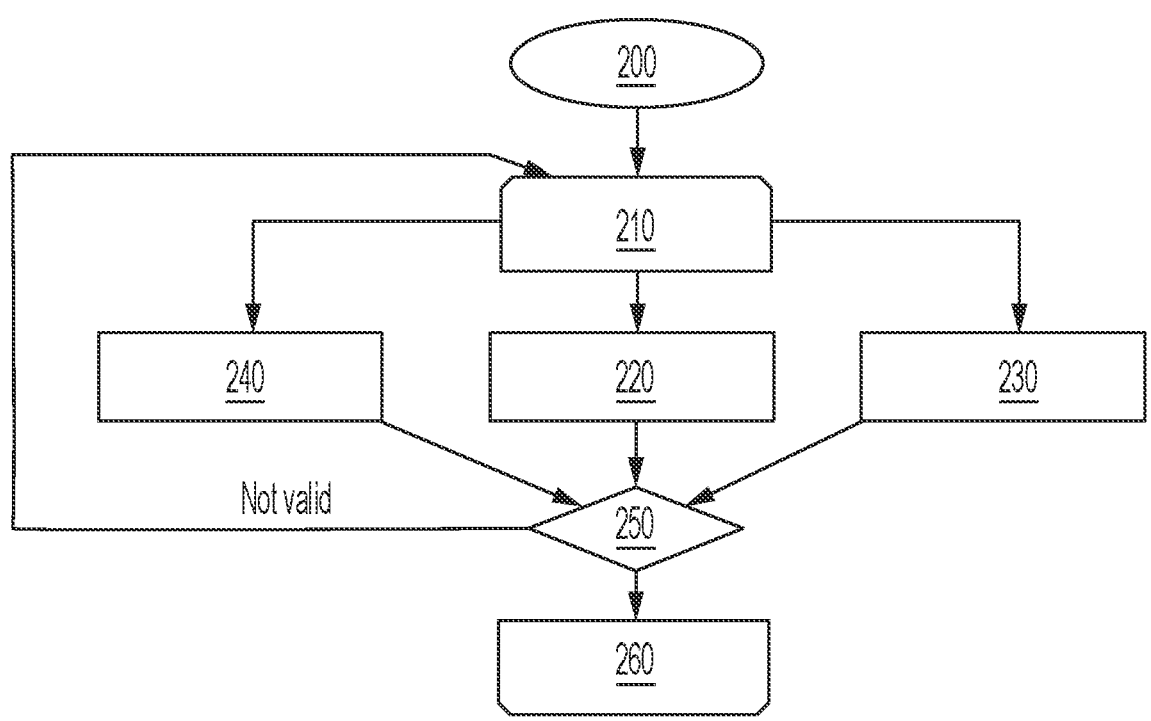
FIG. 5 is a flowchart of a part of a further preferred embodiment according to the present invention relating to the torso analysis from a 3-D image recording.

In step 180, it is determined if the resulting marker from the combination of separate 3-D imaging information recordings is valid. Such validity is obtained if the combined 3-D image recording comprises sufficient information, such as for example performed by analyzing the 3-D imaging information recording starting from the marker position down to the bottom by steps of 3 cm and checking the percentage of holes present in the 3-D photo. Acceptability is for instance defined if the percentage is below 3%. In step 190, the method ends with outputting a validated 3-D photo FIG. 5 describes an embodiment of pre-analysis in preparation for computation during analysis. This phase represents a pre-analysis of this 3-D imaging information recording for extracting information relating to the subject, was information is of assistance in the correction of errors in the 3-D imaging information, the recognition of parts of the subject such as the shoulders, head, breast areas. The purpose of this embodiment is to analyze usability of available information for the extraction of the thorax information relating to the electrode positions. In step 200, the method is initialized by loading the 3-D imaging information and analyzing means, such as a tracker for shoulders. Here, the characteristics of the marker is related to a specific use. A blue marker is for instance used for analyzing the anatomy of the body, such that for instance if the marker is rectangular and its color is plain blue the analysis of the body will be performed relating to the circumference of the torso the width or the circumference of the arm.

Figure 9:
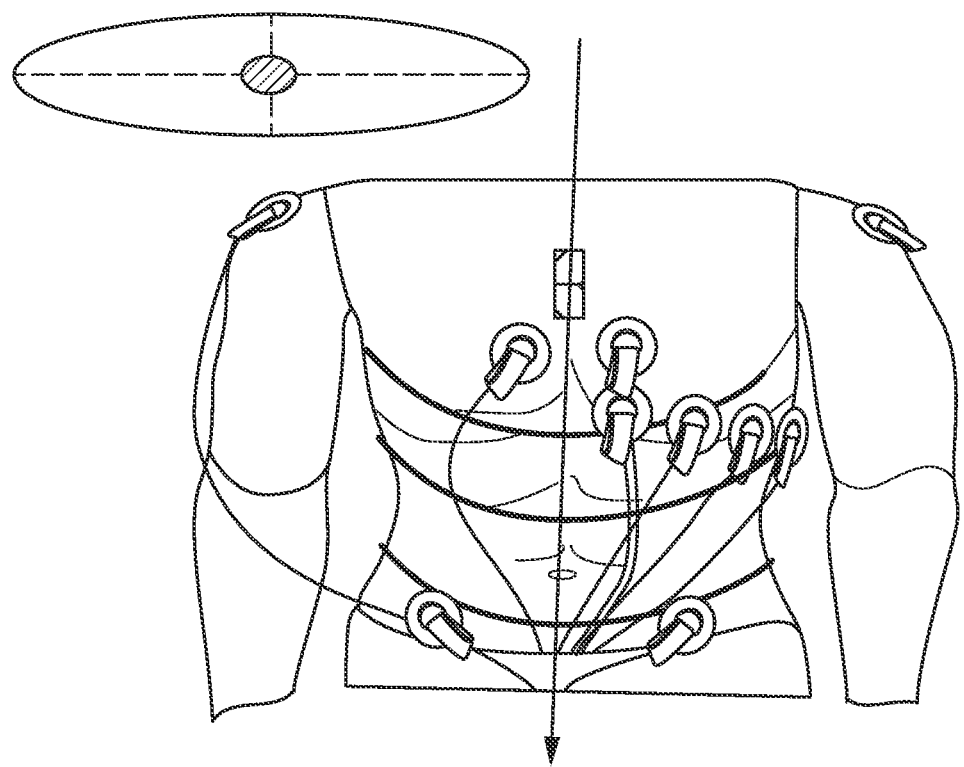
FIG. 9 is one embodiment of the marker element as applied on a torso relative to ECG electrodes also on the torso for performing a method according to a preferred embodiment.

Step 210 comprises loading or detection an anatomical thorax element/parts from the 3D-Photo and categorization those element/parts relating them to their body positions. The detection in this level is a categorization per region relative to the marker position as depicted in FIG. 9.

A coordinate analyzer separates the points of 3-D imaging information to points which are in higher position than the position of the marker then divide this upper part to left and right category. The other points from the 3-D imaging information, preferably having an altitude lower than the marker's altitude, those will be in the list (group) representing the belly.

The detection of the thorax is a combination of information given by specific analyzers. A shoulders analyzer will give the position of the shoulders, a circumference analyzer gives us different circumferences related to an altitude (horizontal position). From those two information we have the upper offset of the thorax and also the left and right is deduced from the ellipse equation of the biggest circumferences found.

Figure 10:
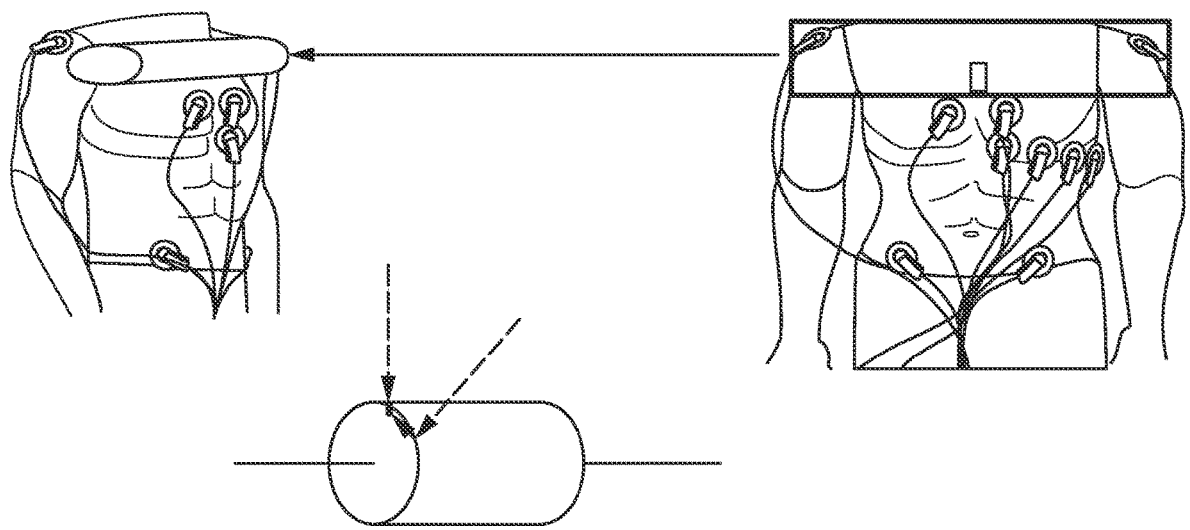
FIG. 10 is an example of using a cylindrical geometry approach to define the shape of the shoulders.

Step 220 is defining the shape of the shoulders, for example using a cylindrical geometry approach, such as shown in FIG. 10. The shoulders analyzer gets lists of points and studies the relations thereof toward each other. In other words, the analyzer search for area where the depth of points decreases progressively for those points to be in the same distance from a line, such as a central axis of the cylinder they form.

In step 230, the circumference of the torso is analyzed. For the detection of the circumference of the torso the symmetry and the variation in the distance of the torso in the same altitude is analyzed. Curved lines are created with points at the same altitude at for instance a 2 cm interval. Ellipses are created in this way for determining the circumference of the torso for permitting the prediction of the dimension of the subject. This prevents manipulation reduction.

In step 240, other characteristics of the torso are determined, such as the head, hair, or skin color. Also elements in the photo that are distracting to analyzing the torso, such as a blanket on the subject, are rejected as much as possible. Preferably, it is known what color blanket is used such that imaging points having the same color as the blanket can be removed from analysis, thereby saving time of analysis by such noisy information.

In step 250, the information from the analyzer is from the steps 220, 230, and 240 are combined to improve the analysis. For example, by knowing the position of the shoulders and the points in the imaging information constituting the shoulders, the central axis of the cylinder that they form helps in detecting borders where the imaging information may end, for example because there are no electrodes beyond such areas.

Figure 6:
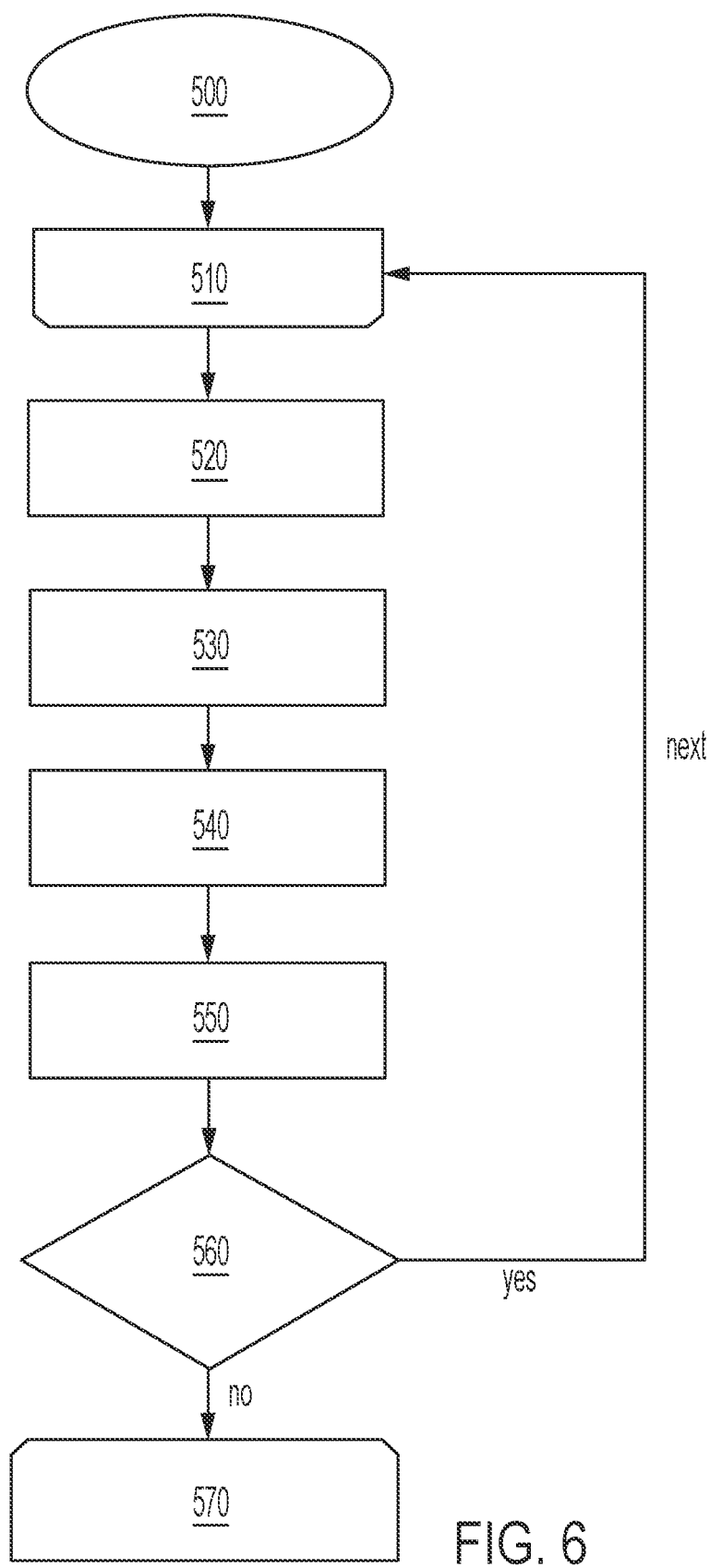
FIG. 6 is a flowchart of a part of a further preferred embodiment according to the present invention relating to an exemplary process of matching a 3-D image recording with a torso model.

FIG. 6 shows a method for matching the 3-D torso model to the 3-D imaging information recording. The method starts in step 500 with loading information, and initializing the computing device for performing the calculations. The input of step 510 is the information relating to the 3-D imaging information recording and the 3-D torso model. The position of the marker element in the imaging information recording as well as its equivalent position in the 3-D torso model is taken as the basis to calculate the difference of distance and the angles created by the kerf of the marker zone in the model and the imaging information.

Step 510 provides: take the marker position and its equivalent position by the model, then calculate the difference of distance and the angles created by the curve of the marker zone in the model and 3D photo.

The coordinate of the marker initially in the 3D photo is expressed in camera space (is the camera which give the point of 3D photo its coordinate) and the marker coordinate in the model is defined by the MRI device as consequence, except coincidence, the position of the marker in the 3D photo and model are different. The positions of the marker and the equivalent of the marker are separate by a distance not null 0, see FIG. 12.

Figure 11:
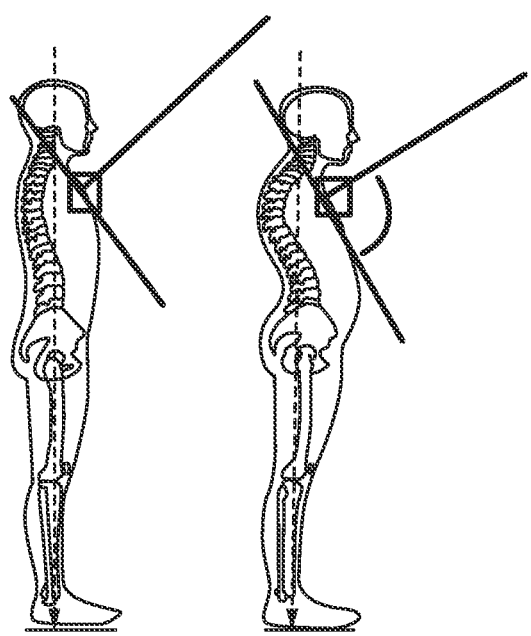
FIG. 11 shows the translation of a 3D photo to model normal vectors of the model until the 3D photo has an angle equal to 0 degrees.

The normal in the position of the marker in 3D photo and in the model are the same. That is why the angles between the should be null as consequence transformation has to reduce that angle to 0, see FIG. 11.

Step 520 provides: the 3D-Photo is moved to the model until the distance of the marker and its equivalent position is reduced to 0.

The distance between the marker in 3D photo and its equivalent position in the model is calculated then the 3D photo is translated to the position of the marker. Indeed we calculate the vector of translation and we move the coordinates of every point of the 3D photo using the calculated vector.

EXAMPLE

A - - - translate->B
A+vector=B
Vector=B−A.
See FIG. 2 and FIG. 13
Step 530 provides: 3D-Photo will be rotated until their curves are positively parallel and control if the distance between the marker and its equivalent position is null, see FIG. 14.

After translating the 3D photo to model the normal vectors (representation of the curve) of the model and the 3D photo must have an angle equal to 0 degree. If is not the case points of 3D photo are rotated until that angle becomes null. See FIG. 11

Step 540 provides: the new update of 3D-Photo is present but that does not grant that the photo and the model are in the same orientation.

Figure 12:
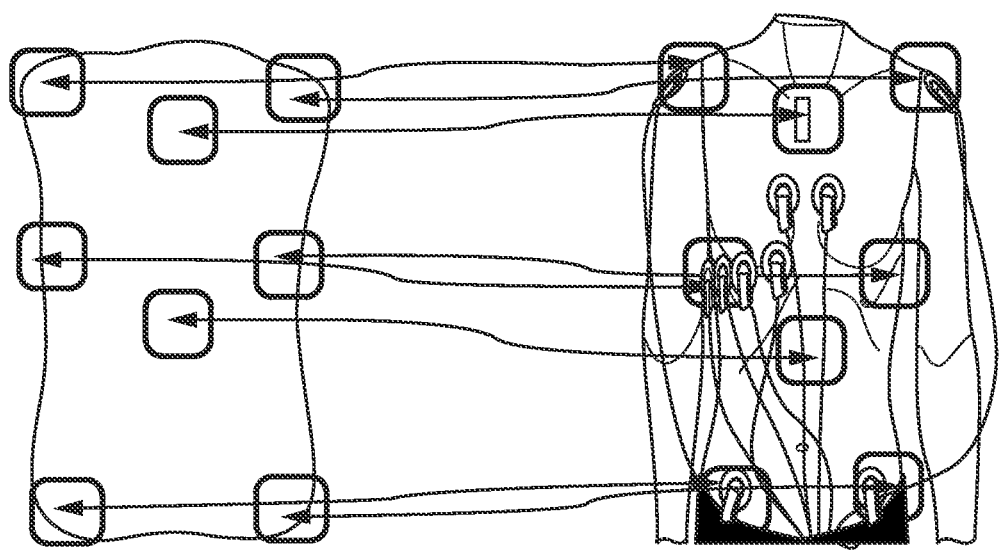
FIG. 12 shows the coordinate of a marker element initially in a 3D photo expressed in camera space and the marker coordinate in a model wherein the position of the marker in the 3D photo and model are different.
Figure 15:
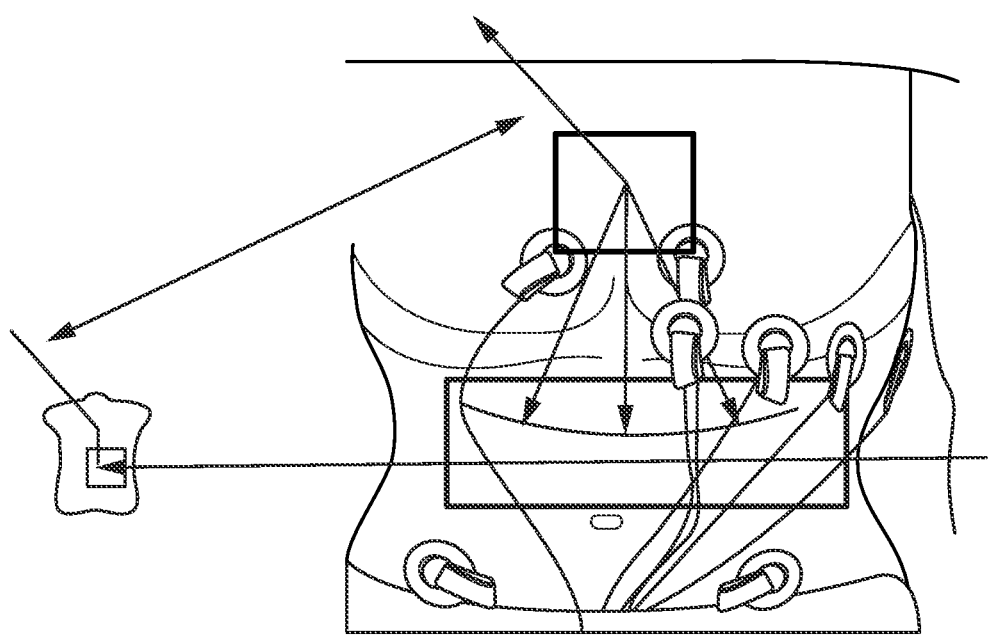
FIG. 15 shows the correction of orientation of a 3D photo and a model by taking two equivalent random zones and calculating two vectors which go from the marker position to that area and rotate the 3D photo until the two points coincide or become equal.

This phase permits the correction of orientation of the 3D-Photo and the model by taking two equivalent random zones and calculation of two vectors which are going from the marker position to that area and rotate the 3D-photo until that two points coincide or become equal, see FIG. 12 and FIG. 15.

Step 550 provides: Estimation of the matching is the calculation of the difference of distance between projection of the element of 3D-Photo and their equivalent from the model.

Figure 16:
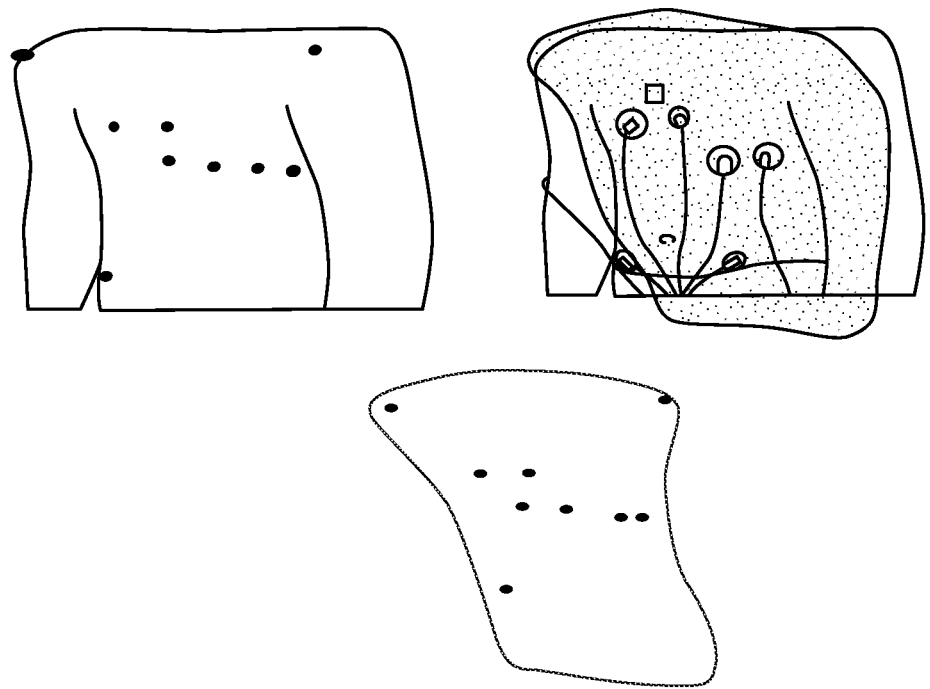
FIG. 16 shows a 3D photo and models used for calculating a difference of distance of every point from the 3D photo and its projection into a model.
Figure 17:
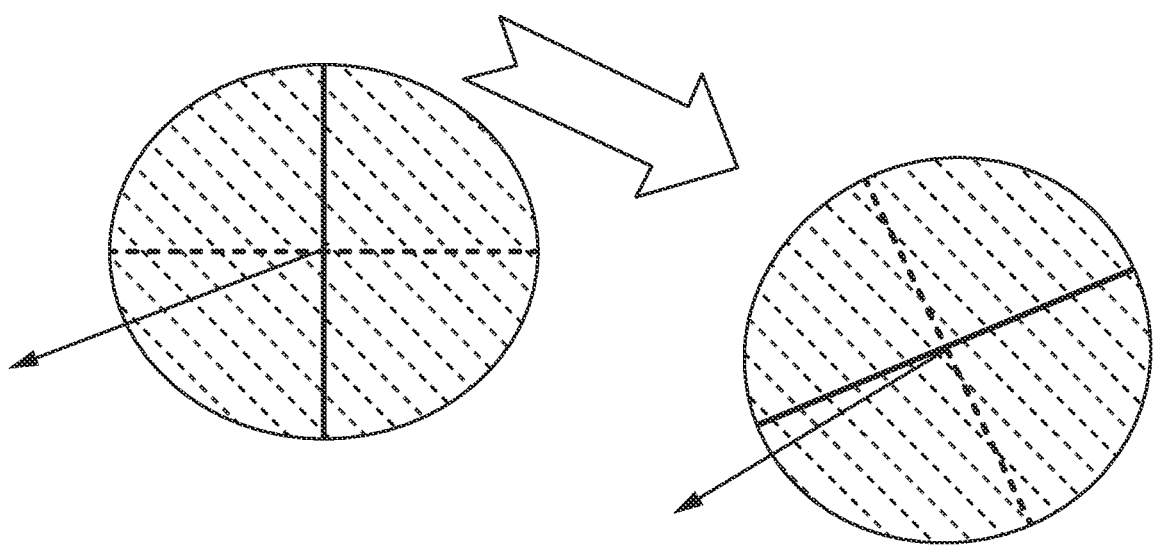
FIG. 17 is an illustration of the calculation of the difference of distance of every point from a 3D photo and its projection into a model.

The following configuration of matching the marker position and a second point which is in 180 millimeter from the marker position is considered. We select a list of second point (random point) which are in same distance from marker in 3D photo then we calculate the transformation every time we select a point from the list of second point. Then the percentage of the difference of distance of every point from 3D photo and its projection into model is calculated and the best percentage is taken after comparing all transformations there are. See FIG. 13, FIG. 16 and FIG. 17.

Step 560 provides: compare with latest estimation if the value increased or not and apply the best transformation. If the percentage increased the calculation will be retried with another configuration until a maximum related to the model and the 3D-Photo is reached.

After step 550 the best percentage relative to the selected list of second point (point from random zone) is obtained. If the current best percentage is better than the old one the estimation improved.

Every time there is improvement the process is reiterated until that every percentage resulting from a selected configuration stays lower that the saved one.

Figure 13:
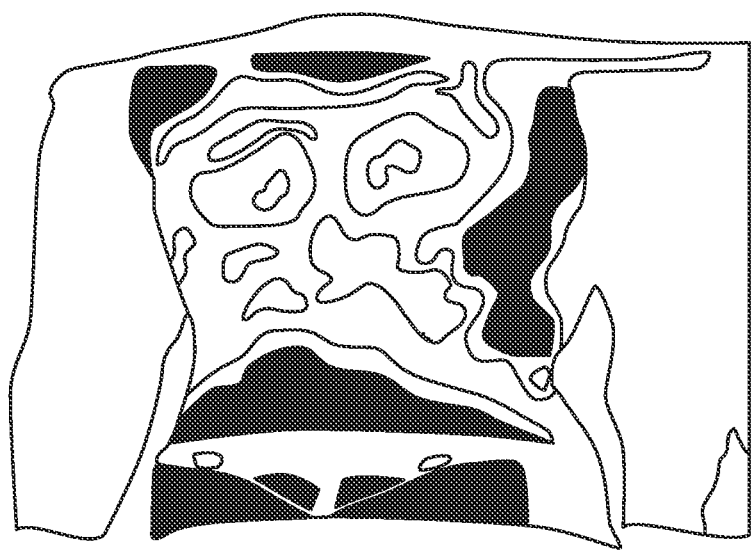
FIG. 13 is a 3D photo of a torso to which a marker element and electrodes may be applied.
Figure 14:
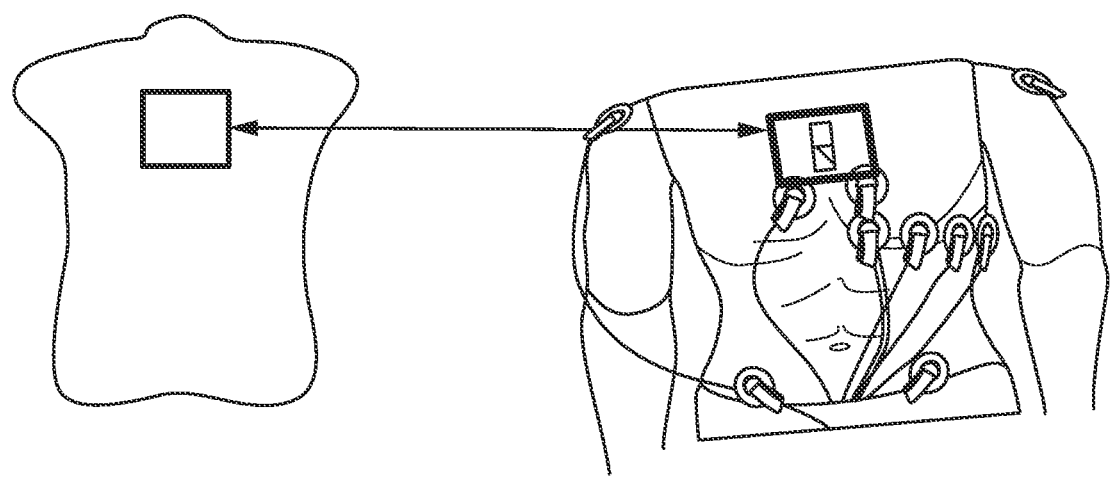
FIG. 14 shows the rotation of a 3D photo until the curves of a marker zone in a torso model and a 3D photo are parallel.
Figure 18:
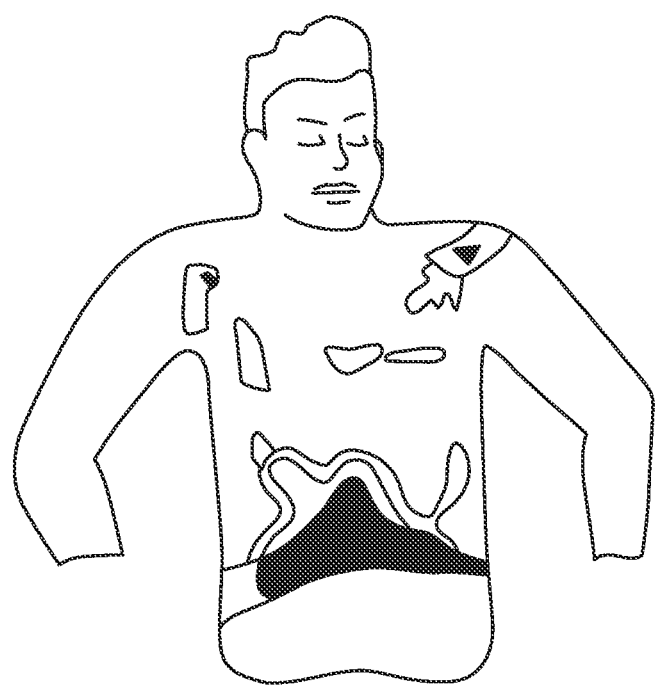
FIG. 18 is a 3D photo of a torso including ECG electrodes on the torso.

By comparing every possibility it is indicated that the best result that can be provided with that 3D photo is obtained, see FIG. 15, FIG. 13 and FIG. 18.

Step 570 provides: the new 3D-photo is stored and can be used to extract the specific information and apply them to the model like electrodes position for example.

Figure 7:
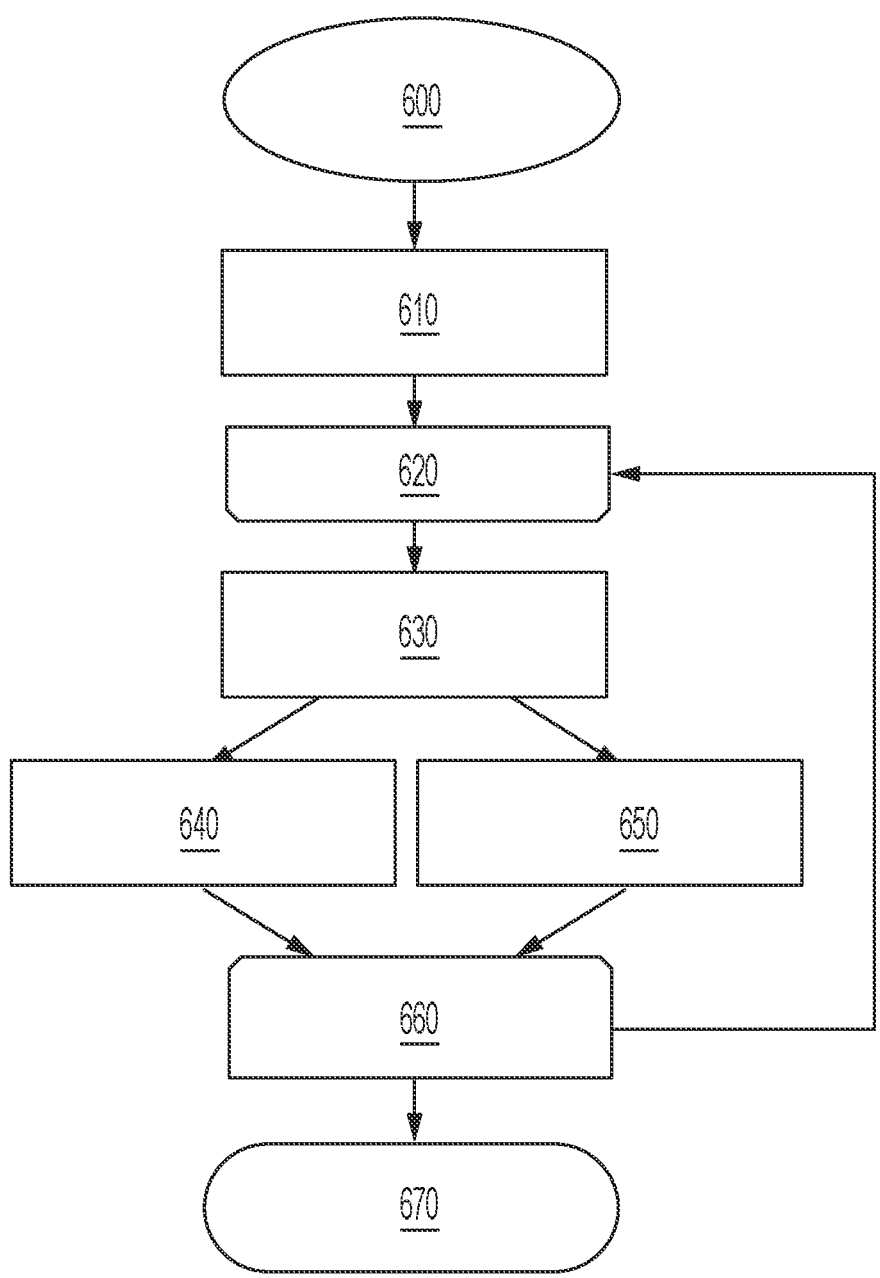
FIG. 7 is a flowchart of a part of a further preferred embodiment according to the present invention exemplifying a further process of matching a 3-D image recording with a torso model.
Figure 8:
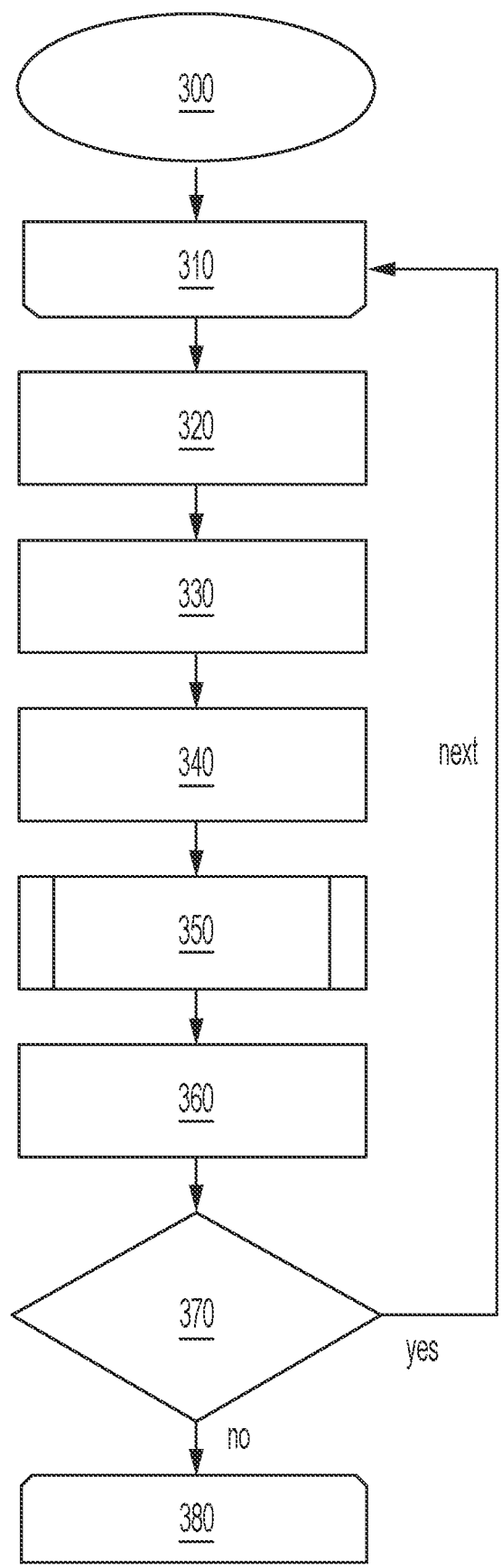
FIG. 8 is a flowchart of a part of a further preferred embodiment according to the present invention relating to the analysis of areas on the 3-D image recording.

FIG. 7 shows a method for analyzing areas on the imaging information recording and defining a coordinate system relative to the marker element.

Step 600 provides: load the 3D-Photo and load the resources needed for the process (load the specific analyzer).

Figure 19:
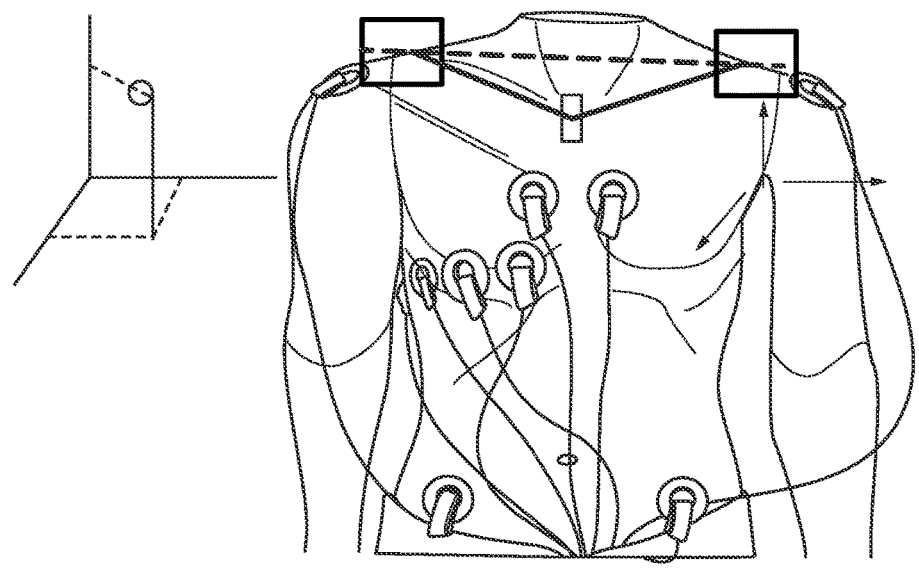
FIG. 19 shows points of a 3D photo positioned relative to a marker.

Step 610 provides: the marker analyzer goes to position of the marker and use the information related to it and creates from those information the "marker" to which every data is related. The points of the 3D photo in the space (coordinates) are positioned related to that marker, see FIG. 19.

Figure 20:
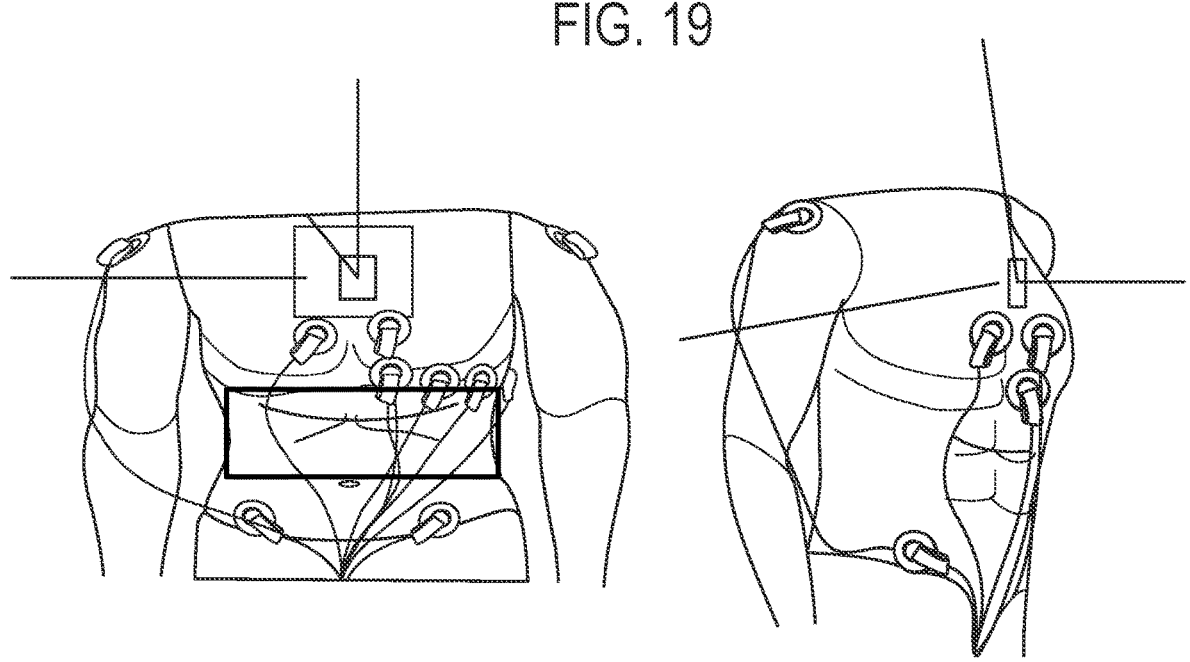
FIG. 20 shows 3D views of 3 axes of a marker to which coordinate(s) of points from the 3D photo may be expressed.
Figure 21:
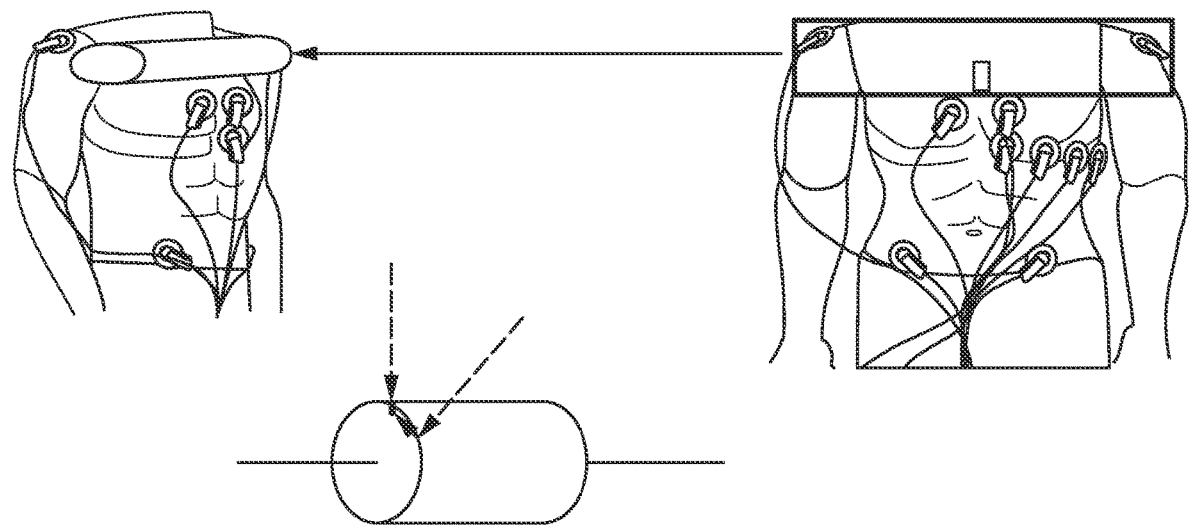
FIG. 21 shows an example of using a cylindrical geometry approach to define the shape of the shoulders.

The marker contains 3 axes to which every coordinate of a points from the 3D photo is expressed, see FIG. 20.

A point is taken from the 3D photo. That point after recording is expressed with the coordinate that the camera gives to that point in one side. In the other one, the coordinate of a point from the model is expressed with the coordinates given by the MRI device. The marker in 3D photo and its equivalent in the model are the same. As consequence, the coordinates are expressed using the same reference.

Step 620 provides: by the start of analyzing using the information generated from "610", the zone of analysis is defined, see FIG. 20.

The zone of analysis is the result of the combination of the information that the analyzers provide. The line of the shoulders is the upper border of analysis. The radius of the biggest circumference plus the ellipse's center of all circumferences provides the offset left and right from the axis formed by the ellipse's center.

Step 630 provides the nearby area (or zone of the analysis) is inspected and is prepared to be categorized to the zone marker or random zone.

An nearby area or the marker zone is the area related to list of points which are close to the marker with a certain distance (3 cm, 5 cm , . . . ). All elements outside of the marker zone are in the random zone or what is called the control zone, see FIG. 14.

The analyzer calculates the curve of the geometry where the marker is positioned. The curve is how the concavity of this zone of the 3D-photo behave, see slide 6

The objective is to find the relation of the points and how the global curvature of the area behaves (manifest) due to the repartition. The result of the analysis of the curve is a normal vector that characterizes the area. For example if the area is plane then the normal(perpendicular vector) of the plane is a representation of the curvature which not changes along that plane. If the area is spherical then the normal is perpendicular to the tangent plane of the sphere in that selected position.

The analyzer get the no marker zone (random area), get their characteristics and store them to use them in matching process. The areas are characterized by their distances, their positions, see FIG. 19, see step 630.

The end analyzing structures the obtained information and store those to use those in further process.

The objective is to have 3D points with the same characteristic from the model and their equivalent in 3D photo (3D point from the model which is 80 millimeter far from the marker) to compare every points and with its equivalents to control the quality of matching, see FIG. 15.

Combine the marker with information and correct if there are errors present.

The present invention is described in the foregoing on the basis of several preferred embodiments. Different aspects of different embodiments can be combined, wherein all combinations which can be made by a skilled person on the basis of this document must be included. These preferred embodiments are not limitative for the scope of protection of this document. The rights sought are defined in the appended claims.

The invention claimed is:

1. A method performed by a computing device part of or coupled to an ECG device for applying a marker element in a process of determining positions of a set of ECG electrodes as placed on a human torso relative to a 3D model of a human body, the method comprising:
    receiving an imaging information recording relating to the human body from an optical 3D imaging device, the optical imaging information comprising:
    imaging information of the exterior of the human torso,
    imaging information of the marker element, the marker element being arranged in an area comprising an actual position of placement thereof on the human body, and
    imaging information of the ECG electrodes as placed on the human torso, and performing an image recognition on the imaging information for obtaining a positive or negative presence determination of the marker element in the imaging information.

2. The method according to claim 1, further comprising making a decision as to usability of the imaging information based on at least the presence of the marker element in the imaging information and/or discernibility thereof.

3. The method according to claim 1, further comprising assessing a quality of one or more predetermined parameters of the imaging information including whether the marker element is in the image, whether the distance of the optical 3D imaging device to the exterior of the human torso or the marker element is within pre-determined limits, whether a portion of the human torso is within the imaging information, or a combination thereof.

4. The method according to claim 1, further comprising subdividing the imaging information recording into analysis areas for performing imaging analysis per analysis area, for determining presence of the marker element, or for determining one or more parameters of the human torso.

5. The method according to claim 1, further comprising receiving a partial imaging information recording of the human torso, analyzing the partial imaging information recording, and making a decision of usability of the partial imaging information recording.

6. The method according to any claim 1, further comprising determining a number of the ECG electrodes in the imaging information recording or a partial imaging information recording.

7. The method according to claim 1, further comprising interpreting a range of imaging information recordings over time during an ECG session.

8. The method according to claim 1, further comprising interpreting information patterns of the marker element, the information patterns comprising a color, a shape or combination of shapes, or a geometrical shape.

9. The method according to claim 8, wherein the information patterns comprise optically discernible indication elements, including information elements providing directional information, for indicating directions from the marker element in which elements of the human body are to be recognized or in which one or more of the set of ECG electrodes are to be placed on the human torso.

10. The method according to claim 8, wherein the information patterns comprise optically discernible indication elements, including information elements providing directional information, for indicating directions from the marker element in which projections towards the body are to be performed.

11. The method according to claim 8, wherein the information patterns comprise an optical code, a bar code, a pattern code, or a QR type code.

12. The method according to claim 1, further comprising interpreting a light emitted from a light emitting element of the marker element.

13. The method according to claim 1, further comprising interpreting a sound emitted from a sound emitting element of the marker element.

14. The method according to claim 1, further comprising interpreting an RF signal emitted from an RF emitting element from the marker element.

15. The method according to claim 1, further comprising determining a marker element origin relative to the marker element, the marker element origin defining a marker element coordinate system in which a predefined point of the marker element is the origin or in which the predefined point of the marker element is defined outside the origin.

16. The method according to claim 1, further comprising:
receiving a torso model of the body from a storage, or from a body scanning imaging device comprising an MRI, CT, PET-CT, or an ultrasound device, or from a database of standardized models,
performing a model matching operation resulting in matching determination data of the torso model of the body relative to the imaging information recording based on an initial position determination of the marker element relative to the human body, and
storing position determination data resulting from the model matching operation.

17. The method according to claim 1, further comprising:
receiving as part of the imaging information recording imaging information about the set of ECG electrodes,
performing a position determining resulting in position determination data of the position of at least one of the set of ECG electrodes relative to a torso model of the body and/or the human body based on an initial position determination of the marker element relative to the human body, and
storing the position determination data.

18. The method according to claim 17, further comprising rendering the position determination data for displaying on a display screen.

19. The method according to claim 15, further comprising relating a model coordinate system to the marker element coordinate system, and providing translation relation therebetween or a location of the marker element in a torso model of the body.

20. The method according to claim 16, further comprising:
relating position information about the marker element to the torso model of the body,
relating position information about the set of ECG electrodes to the torso model of the body, and
using the relation position information to augment the torso model of the body with the position information about the set of ECG electrodes.

21. A marker element for use in the method according to claim 1, the marker element being for placement on an exterior of the human body, the marker element comprising:
a member for taking image recordings thereof for placement on the body, and
a recognition pattern for recognition thereof during an ECG session.

22. The marker element according to claim 21, further comprising graphical patterns for recognition thereof defining the human body in areas in which ECG lead locations are to be expected or recognized.

23. The marker element according to claim 21, further comprising means for emitting a sound or light.

24. The marker element according to claim 21, further comprising an RFID chip.

25. A non-transitory computer readable storage medium comprising computer executable instructions performed by a computing device part of or coupled to an ECG device for applying a marker element in a method of determining positions of a set of ECG electrodes as placed on a human torso relative to a 3D model of a human body, the method comprising:
receiving an imaging information recording relating to the human body from an optical 3D imaging device, the optical imaging information comprising:
imaging information of the exterior of the human torso, imaging information of the marker element, the marker element being arranged in an area comprising an actual position of placement thereof on the human body, and imaging information of the ECG electrodes as placed on the human torso, and performing an image recognition on the imaging information for obtaining a positive or negative presence determination of the marker element in the imaging information.

26. A computing device comprising a processor, a coupling means for coupling with an ECG device, a coupling means for coupling with a 3-D camera, and a memory, wherein the memory comprises non-transitory computer executable instructions for the processor to control the computing device, wherein the computer executable instructions comprise instructions for performing a method of determining positions of a set of ECG electrodes as placed on a human torso relative to a 3D model of a human body, the method comprising:

receiving an imaging information recording relating to the human body from an optical 3D imaging device, the optical imaging information comprising:

imaging information of the exterior of the human torso, imaging information of the marker element, the marker element being arranged in an area comprising an actual position of placement thereof on the human body, and imaging information of the ECG electrodes as placed on the human torso, and performing an image recognition on the imaging information for obtaining a positive or negative presence determination of the marker element in the imaging information.

\* \* \* \* \*